United States Patent

Vanmoor

[11] Patent Number: 5,707,967
[45] Date of Patent: Jan. 13, 1998

[54] PAIN RELIEF COMPOSITIONS

[76] Inventor: Arthur Vanmoor, 153 E. Palmetto Park Rd. #219, Boca Raton, Fla. 33432, now by change of name from Arthur Van Moerkerken

[21] Appl. No.: 549,649

[22] Filed: Oct. 27, 1995

[51] Int. Cl.[6] .................. A61K 38/05; A61K 31/235; A61K 31/195

[52] U.S. Cl. ................. 514/19; 514/533; 514/561; 514/562; 514/564; 514/565

[58] Field of Search .................. 514/561, 562, 514/564, 565, 533, 19

[56] References Cited

U.S. PATENT DOCUMENTS

| | | | |
|---|---|---|---|
| 5,395,612 | 3/1995 | Griffith et al. | 424/94.6 |
| 5,500,226 | 3/1996 | Stroppolo et al. | 424/466 |
| 5,576,351 | 11/1996 | Yoshimura et al. | 514/565 |

*Primary Examiner*—William R. A. Jarvis
*Attorney, Agent, or Firm*—Otto S. Kauder

[57] ABSTRACT

Disclosed are compositions containing either aspartame or monosodium glutanate combined with an amino acid.

18 Claims, 2 Drawing Sheets

5,707,967

PAIN RELIEF COMPOSITIONS

This invention relates to the relief of pain. More particularly, this invention relates to the relief of pain generally deemed (by others than the sufferer) mild to moderate, such as headache, muscle ache, low back pain, arthralgia and the like for relief of which the so-called minor analgesics such as aspirin, acetaminophen, and ibuprofen are conventionally recommended. These minor analgesics are believed to have helped many people and are consumed in large quantities worldwide. They are, however, not free of unpleasant and even dangerous side effects, and new and improved remedies are constantly being sought.

As pointed out by W. Michne (Encyclopedia of Chemical Technology, third edition, vol. 2, pages 574–586), "the search for new, more effective analgesics and anti-inflammatory agents with fewer and/or less severe side effects is a continual endeavor, and promising agents are ultimately (emphasis added) studied in man. The laboratory and clinical evaluations of new drugs are complex disciplines . . . " The writer implies that before a "promising agent" is studied in man, it must be established by testing with animals that administration to humans is safe, and that the agent offers at least some promise of mitigating human pain. While methods of evaluating safety are well known, study of analgesic effectiveness in experimental animals is not straightforward and remains a controversial subject, especially with respect to correlation of effects in animals and in humans.

J K Saelens and F R Granat ("New Drug Discovery and Development", pages 263-) have described a "phenylquinone writhing test in mice" that is sensitive to all known analgesics and therefore deemed an excellent primary screening test for new candidates. Male mice receive intraperitoneally 0.1 ml/10 g body weight of an 0.25 mg/ml solution of phenyl-p-quinone in 5% aqueous ethanol. Five minutes later they are placed in observation cages and the number of animals which do not perform a characteristic writhe during the next 10 minutes are recorded. The authors found that phenylquinone induces one or more writhes in 95% of the injected mice. Test compounds are then administered and evaluated for their effectiveness in inhibiting the characteristic writhe response to phenylquinone.

While this is only one test method of many that have been proposed, it serves to illustrate the laboriousness and complexity of the effort required. Yet this effort is merely that of one stage in the process, i.e. that of the primary screening for activity. For an overview of the entire process from the proposal of an idea by a researcher to the initiation of clinical trials of a remedy, reference can be had to "Natural History of a Typical Drug" a chapter by Dr. E. L. Harris in "The Principles and Practice of Clinical Trials" (Harris and Fitzgerald, editors, E. & S. Livingstone, Edinburgh and London, 1970). Harris writes "The first stage is that of the idea. Whatever the source of the idea, it is considered by a research panel consisting of medical, chemical, pharmacological, pharmaceutical and commercial interests. If the panel feel that the idea has merit, then the research chemist sets about synthesising the compound or a number of related compounds. This can be a very long and arduous task; it has been estimated that synthesis and initial biological screening of a single compound can take up to 400 man hours to achieve . . . .

When sufficient quantities have been made the pure drugs are handed over to the pharmacologist who carries out a programme of empirical screening tests, designed to cover as wide a range of pharmacological actions as economically as possible so as to expose any effects which might be of therapeutic use. If an anction is detected more detailed experiments to elucidate this are carried out.

Many compounds are rejected at this stage either because of lack of activity or gross toxicity. Those that do survive are again considered by the research panel who decide whether the agent has sufficient promise to go forward to assess its safety in animals.

There are three phases in toxicity testing. The first is the acute toxicity study which deals with the quantitative assessment of the short term effects of a drug. The response is noted after a single oral or parenteral dose, or several doses given within 24 hours. These tests are carried out in a variety of species.

The next is sub-acute toxicity, and in general covers repeated dosage in at least two species, such as mice and rats, for periods up to 90 days. An additional non-rodent species, eg. dog, is often included.

Chronic studies are for the duration of life in the animal—rats and mice are suitable. Occasionally long term studies are employed in other animals such as dogs and monkeys for periods up to two years . . . .

When the exacting toxicological studies are completed and the research panel is satisfied with all the data that has been generated, the drug is administered to healthy volunteers . . . "

Application of these and similar methods has led to a number of successful products in the field of major analgesics, i.e. substances that mimic the pain relieving effectiveness of morphine with reduced tendency to physical dependence. However, there have been fewer successes in the field of the so-called minor analgesics similar to aspirin. Clearly, in this field there remains a need for improved agents as well as improved techniques for their discovery.

SUMMARY OF THE INVENTION

In accordance with this invention, I have found that I can reproducibly cause a susceptible human subject to experience perceptible pain within a short period of time upon the oral administration of a sufficient quantity of any of a class of substances which I propose to call trigger substances. These trigger substances are in widespread consumer use and are without effect on the great majority of the human population. In a susceptible subject, such as myself, however, the effect is both reproducible and sufficiently long lasting to serve as research tool for the evaluation of agents effective in relieving pain. Accordingly, the method of determining the effectiveness of an agent for the relief of pain comprises the steps of a) administering to a susceptible subject a quantity of a trigger substance reproducibly effective in producing within a period of thirty minutes to a few hours a perceptible sensation of pain lasting for at least ten hours in the absence of treatment.

b) administering to said subject having received said quantity of trigger substance a predetermined quantity of the agent whose effectiveness is to be determined.

c) measuring the duration of said sensation of pain upon administering said agent, and d) comparing the durations of said sensation with and without the administration of said agent.

Also in accordance with this invention, I have found that effective quantities of certain nutrient substances can reproducibly relieve pain produced in a susceptible subject by the administration of a trigger substance in less time than required by a conventional remedy such as aspirin. Being nutrient substances that are ingested and metabolized by humans daily. such substances are inherently safe. Accordingly, the method of relieving pain in a person in need of such relief, comprises the administration to such person of a quantity of an agent determined to be effective in relieving pain by the method of this invention. Such administration of an agent can take place after the administration of a trigger substance, at the same time as a trigger substance is administered, or even before a trigger substance is administered, so that the sensation of pain that would be produced without the agent is thereby prevented.

Also in accordance with this invention, I have found that an agent found effective in accordance with this invention in relieving pain can be combined with a trigger substance to prevent or eliminate the tendency of such trigger substance to produce sensation of pain in a susceptible individual. Such a combination of effective agent and trigger substance can be usefully marketed to populations of consumers that include susceptible individuals, to afford such individuals the benefits associated with the trigger substance without its undesirable accompanying effect of causing pain.

Also in accordance with this invention, I have found that an agent found effective in accordance with this invention in relieving pain can be combined with a pharmaceutically acceptable carrier to provide an effective palatable pain relief remedy composition. Moreover, I have found that a combination of two or more selected agents found effective in accordance with this invention in relieving pain can be combined with a pharmaceutically acceptable carrier to provide a pleasant tasting as well as effective and palatable pain relief remedy composition.

DESCRIPTION OF PREFERRED EMBODIMENTS

Trigger Substances

Figure 1:
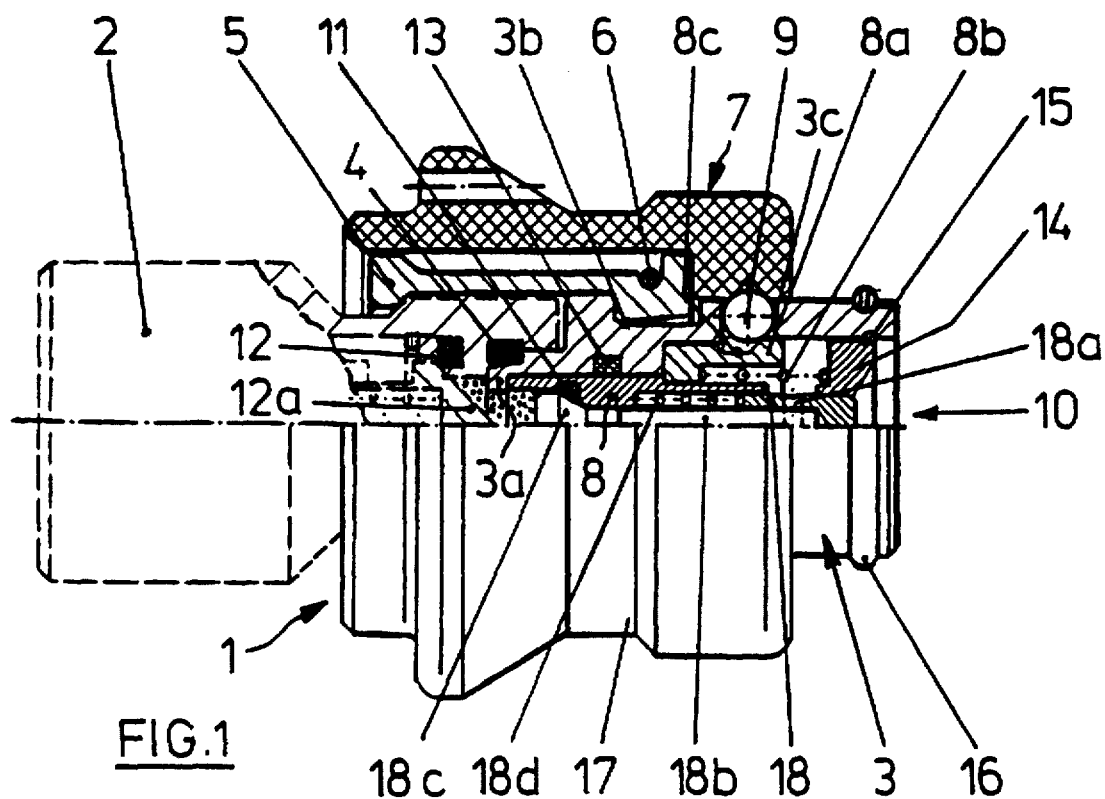
Figure 2:
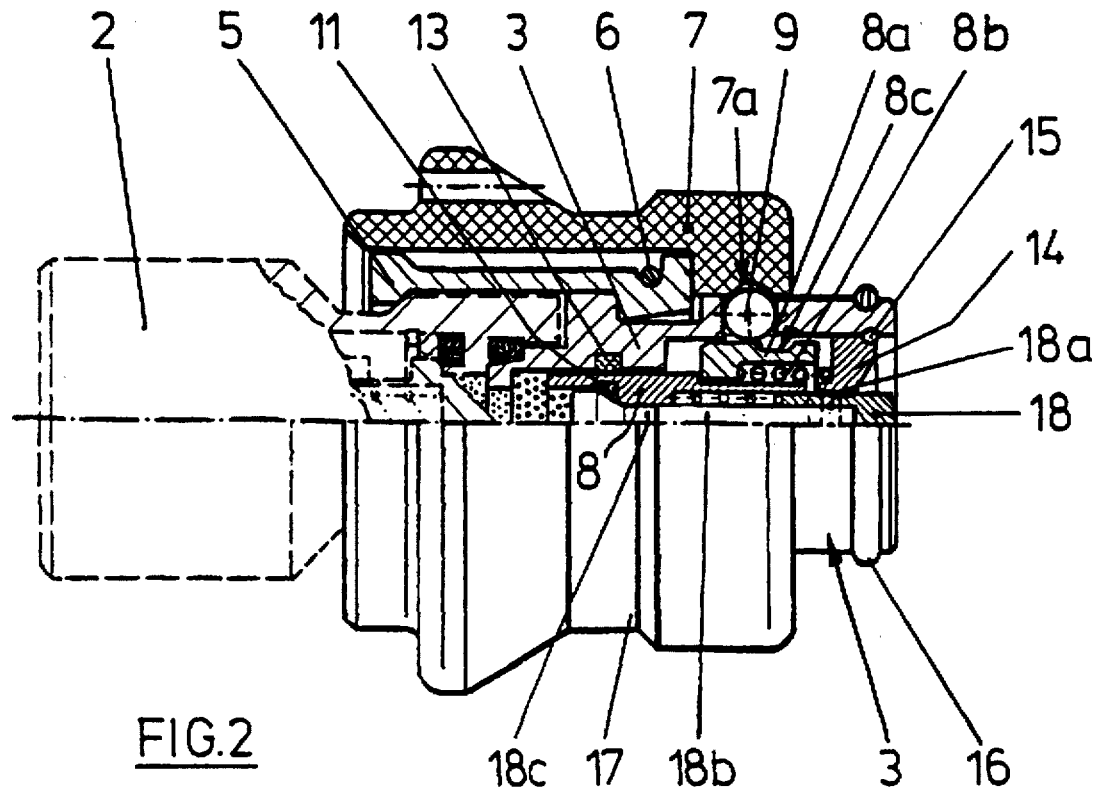
Figure 3:
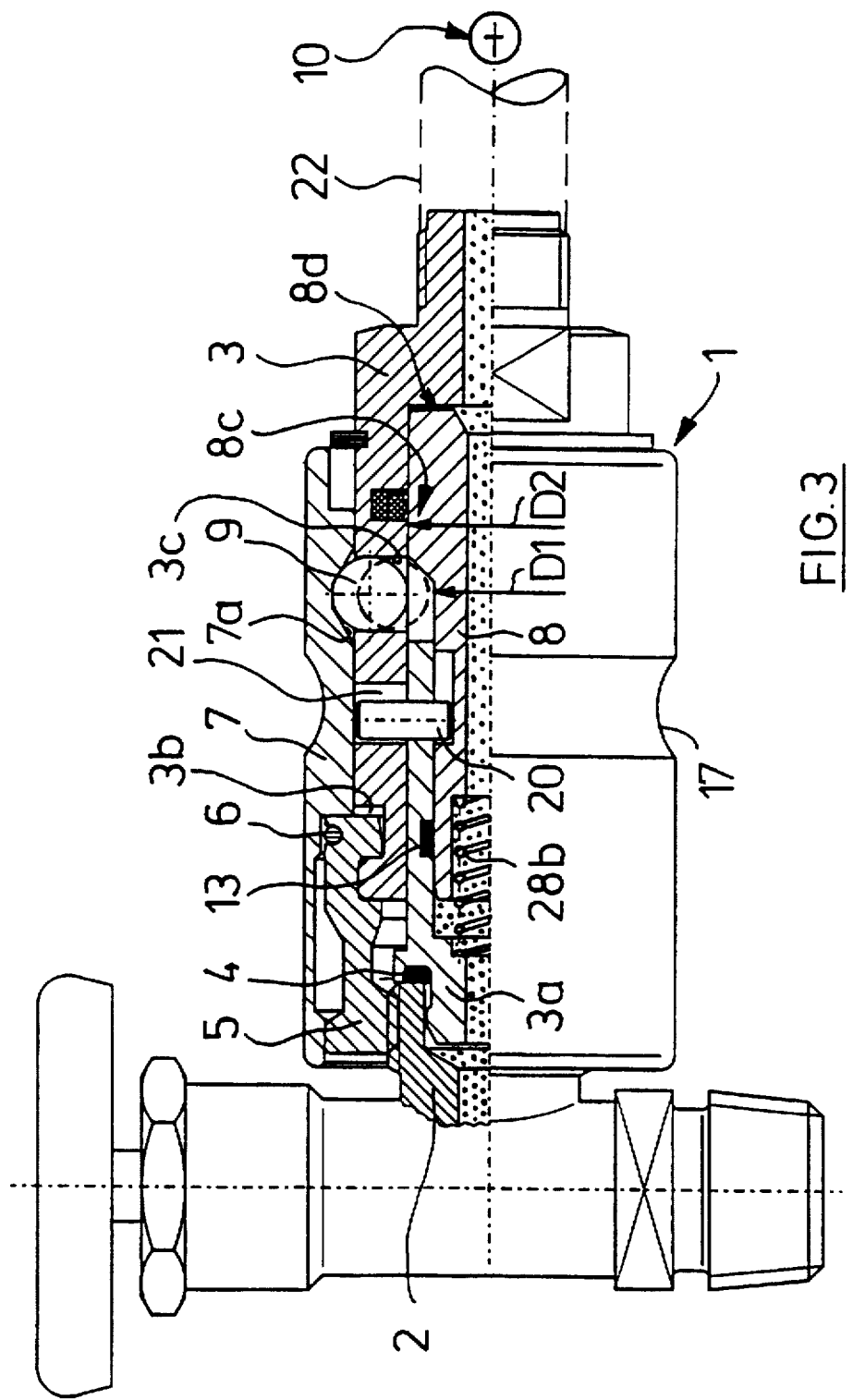

A trigger substance according to this invention is defined as any substance that, when administered to a susceptible human subject, reproducibly gives rise to a sensation of pain in such subject in a time period of thirty minutes to a few hours. Preferred trigger substances are those known to be safe to administer to a human subject, particularly substances known to be in consumer use or authoritatively regulated for such use under observance of appropriate limitations. Included among such trigger substances are substances commonly added to foods in order to modify their taste; this category of taste-modifiers embraces non-nutritive sweeteners including (but not limited to) saccharin, aspartame, and acesulfame-K as well as flavors and flavor enhancers including (but not limited to) acetoin, anethole, benzaldehyde, cinnamaldehyde, ethyl vanillin, methyl anthranilate, monosodium glutamate, and vanillin; additional categories of trigger substances are preservatives including (but not limited to) phenols such as butylated hydroxyanisole and butylated hydroxytoluene, benzoate compounds such as ammonium benzoate, potassium benzoate, sodium benzoate, and benzoic acid, sulfite compounds such as potassium bisulfite, potassium metabisulfite, sodium bisulfite, sodium metabisulfite, sulfur dioxide, and sulfurous acid, and sorbate compounds such as potassium sorbate, sodium sorbate, and sorbic acid; and pesticides and pesticide residues permitted to be present in or on food including (but not limited to) Captan, Chlorpyrifos, Diazinon, Diquat, Glyphosate, Malathion, Paraquat, pyrethrins, and Thiabendazole.

Trigger substances can also include whole products in which it may or may not be possible to identify a particular ingredient as responsible for the trigger effect. Such products include diet carbonated beverages, identified by their effect differing from that of similar beverages formulated with nutritive sweetener; whether the trigger substance in such diet beverages be the non-nutritive sweetener contained therein, or the preservative contained therein, or a combination of both, or neither of these, is less important than that a reproducible trigger effect has been observed. Another such whole product is beer imported into the United States, of which brands imported from Europe, Japan, and Latin America have been observed to have a reproducible trigger effect while brands brewed in the United States have less effect.

Reproducible pain sensations noted by a susceptible individual upon ingestion of a trigger substance include (but are not limited to) headache, stomach cramps, nausea, tearing eyes, and fits of coughing or sneezing.

The quantitity of trigger substance to be administered for pain sensation to be reproducible is readily determined empirically. For example, a reproducible headache has been noted by a susceptible individual upon consumption of two twelve ounce cans of diet cola beverage, and upon consumption of one twelve ounce bottle of imported beer on an empty stomach.

Agents Effective in Relieving Pain

In accordance with this invention, any desired agent can be tested for its effectiveness in shortening the duration of pain produced in a susceptible individual by administration of a trigger substance. The only limitation is the practical requirement of not doing harm to such individual. For that reason, I have sought effective agents principally among substances known to be safe to administer to a human subject, particularly substances known to be nutrients ingested and metabolized by human beings on a daily or at least frequent basis. I have tested many nutrient substances and found effective among these a restricted group of water soluble aminocarboxylic acid compounds at dose levels in the range from 200 to 20000 milligrams. I use the term water soluble to refer to a solubility of at least three grams in 100 ml of water at 25° C.

A preferred group of water soluble aminocarboxylic acid compounds effective according to this invention in relieving pain can be represented by formula (I):

$$X-(CH_2)_n-CH(O)_qH-CH-COO^- \quad \text{(I)}$$
$$|$$
$$(NH_2^+)_pH$$

in which X is selected from the group consisting of

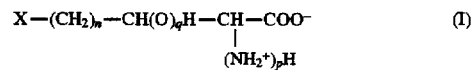

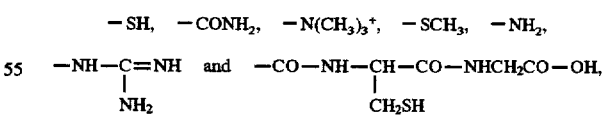

n is zero, one, two, or three, and p and q are each zero or one, provided that p is zero and q is one only when X is $-N(CH_3)_3+$.

Table 1 which follows includes particularly preferred water soluble aminocarboxylic acid compounds represented by formula (I) which I have found effective in relieving pain when administered after administering a trigger substance and in preventing pain when administered before administering a trigger substance.

TABLE 1

| # | Name | X | n | p | q |
|---|------|---|---|---|---|
| 1 | 2-amino-3-mercapto-propanoic acid | —SH | 0 | 1 | 0 |
| 2 | 2-amino-4-carbamoyl-butanoic acid | —CONH$_2$ | 1 | 1 | 0 |
| 3 | 2-amino-4-methylthio-butanoic acid | —SCH$_3$ | 1 | 1 | 0 |
| 4 | 2,5-diaminopentanoic acid | —NH$_2$ | 2 | 1 | 0 |
| 5 | 2,6-diaminohexanoic acid | —NH$_2$ | 3 | 1 | 0 |
| 6 | 2-amino-5-guanido-pentanoic acid | —NH—C=NH<br>        \|<br>        NH$_2$ | 2 | 1 | 0 |
| 7 | 2-(4-amino-5-carboxypentano-amido)-3-mercapto-N-carboxymethylpropanoamide | —CO—NH—CH—CO—NHCH$_2$CO—OH<br>                \|<br>                CH$_2$SH | 1 | 1 | 0 |
| 8 | 3-hydroxy-4-trimethyl-ammoniobutanoate | —N(CH$_3$)$_3$$^+$ | 1 | 0 | 1 |

Formula (I) and all the effective compounds listed in Table 1 contain an assymetric carbon atom and hence exist in non-superimposable optically active forms (so-called D and L forms) and in racemic mixtures or DL forms. Both D and L forms of the effective compounds and racemic mixtures thereof are contemplated in accordance with this invention.

There is nothing about the structures of the effective compounds of this invention or their known nutrient properties that would have enabled one to predict their effectiveness in relieving pain in accordance with this invention. This unpredictability is further underscored by the finding that a number of aminocarboxylic acid compounds structurally similar to those effective according to this invention but not structured according to formula (I) are ineffective. In Table 2 following, there are listed a number of aminocarboxylic acid compounds found ineffective in relieving pain when administered after administration of a trigger substance. Some of these compounds can be represented by formula (II)

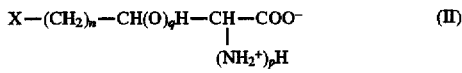

$$X-(CH_2)_n-CH(O)_qH-CH-COO^-\quad\quad (II)$$
$$\quad\quad\quad\quad\quad\quad\quad\quad\quad\quad |$$
$$\quad\quad\quad\quad\quad\quad\quad\quad\quad(NH_2^+)_pH$$

in which the assignments of X and/or n differ from those in formula (I)

TABLE 2

| # | Name | X | n | p | q |
|---|------|---|---|---|---|
| A | 2-aminopropanoic acid | hydrogen | 0 | 1 | 0 |
| B | 2-amino-3-phenylpropanoic acid | phenyl | 0 | 1 | 0 |
| C | 2-amino-3-imidazolyl-propanoic acid | imidazolyl | 0 | 1 | 0 |
| D | 2-aminoacetic acid | not applicable | not applicable | | |
| E | 2-aminopentanedioic acid | —COOH | 2 | 1 | 0 |

While these substances are ineffective as pain relievers, they are not trigger substances and thus can be present in modest amounts as companion substances to effective agents according to this invention. In this way such substances can contribute to the useful properties of the effective agents by enhancing their speed of action, palatability and/or taste characteristics. When present as companion substances to effective agents their concentration will typically range from 1 to 10 weight percent of the effective agent.

Taste Modifying Compositions

Also in accordance with this invention, a taste-modifying material that is a trigger substance in a susceptible individual can be combined with effective amounts of an effective agent according to this invention to provide a taste modifying composition with reduced tendency to produce a perceptible sensation of pain in a susceptible person. Accordingly, taste-modifying materials according to this invention comprise at least one taste-modifying substance able to provoke perceptible pain in a susceptible individual and an effective amount of an effective agent according to this invention. Preferably the effective agent is an aminocarboxylic acid nutrient compound having formula (I). Particularly preferred effective agents are those listed in Table 1.

In the preferred taste-modifying compositions of this invention, any of the above recited taste modifying substances can be combined with any one or more of the effective aminocarboxylic acid nutrient compounds having formula (I). Particularly preferred examples include Saccharin combined with each of compounds #1, 2, 3, 4, 5, 6, 7, and 8 of Table 1.

Aspartame combined with each of compounds #1, 2, 3, 4, 5, 6, 7, and 8 of Table 1.

Monosodium glutamate combined with each of compounds #1, 2, 3, 4, 5, 6, 7, and 8 of Table 1.

In the particularly preferred examples of taste-modifying compositions according to this invention, the relative proportions of taste modifying substance to effective aminocarboxylic acid nutrient compound can range from 9:1 to 1:9 by weight.

Palatable Oral Dosage Forms

Also in accordance with this invention, a pharmaceutically acceptable carrier can be combined with effective amounts of an effective agent according to this invention to provide a palatable oral dosage form for administering to a person in need of sensation of pain relief. Accordingly, palatable oral dosage forms according to this invention comprise at least one pharmaceutically acceptable carrier and an effective amount of an effective agent according to this invention. Preferably the effective agent is an aminocarboxylic acid nutrient compound having formula (I). Particularly preferred effective agents are those listed in Table 1.

One preferred palatable oral dosage form according to this invention is a tablet. A particularly preferred tablet according to this invention comprises a high percentage of at least one aminocarboxylic acid nutrient compound having formula (I) and minor amounts of carrier material acting as binder for the tablet. Suitable binder materials include naturally occurring carbohydrates such as cellulose, starch, galactomannan, fructose, lactose, and sucrose; finely divided ingestible mineral substances such as calcium and magnesium carbonates, calcium and magnesium silicates, calcium and magnesium phosphates, alumina hydrates and hydrotalcite; waxy materials such as beeswax, stearin, stearates of calcium, magnesium, and aluminum, microcrystalline wax and paraffin, and mixtures thereof.

Another preferred palatable oral dosage form according to this invention is a capsule. Capsules have the advantage of delivering the effective agent directly to the alimentary canal without being tasted in the mouth. Suitable capsules are commercially available and are typically made of gelatin, but any sufficiently pure water soluble polymer can be used. Preferably the capsule is filled with the pure aminocarboxylic acid nutrient compound having formula (I); alternatively, suspensions of aminocarboxylic acid nutrient compound having formula (I) in a liquid carbohydrate such as corn syrup or honey, or in a lipid such as lecithin or canola oil can be encapsulated.

A further palatable oral dosage form according to this invention comprises an effective amount of an effective agent according to this invention in a liquid carrier such as a fruit flavored drink. Preferably the effective agent is an aminocarboxylic acid nutrient compound having formula (I). Particularly preferred effective agents are those listed in Table 1.

Suitable fruit flavored drinks include natural fruit juices such as pineapple juice, apple juice, grape juice, orange juice, grapefruit juice, cranberry juice, and mixtures thereof; reconstituted juices prepared from water and fruit juice concentrates, and fruit juice drinks containing water and at least 10% of natural fruit juice.

In oral dosage forms according to this invention, the proportions of carrier to effective agent can vary over a broad range in accordance with the kind of carrier selected and the strength desired. Thus the proportion of carrier can be as little as 0.1% by weight, as in a tablet, and as high as 85% or even more, as in a fruit flavored drink.

Tablets in accordance with this invention can be prepared, for example, from 750 milligrams of each of compounds #1, 3, 5, 7, and 8 of Table 1 and 5 milligrams each of stearin, magnesium stearate, and magnesium silicate.

Capsules in accordance with this invention can be prepared, for example, by filling elliptical capsules of 1.5 ml capacity with 500 milligrams of each of compounds #1, 2, 3, 4, 5, 6, 7, and 8 of Table 1.

Fruit flavored drinks in accordance with this invention can be prepared, for example, from 3750 milligrams of each of compounds #1, 2, 3, 4, 5, 6, 7, and 8 of Table 1 and 75 milliliters of commercially available apple-cranberry drink.

Pleasant Tasting Oral Dosage Forms

Also in accordance with this invention, a pharmaceutically acceptable carrier can be combined with effective amounts of an effective agent according to this invention and a flavorant to provide a pleasant tasting oral dosage form for administering to a person in need of sensation of pain relief. Accordingly, pleasant tasting oral dosage forms according to this invention comprise at least one pharmaceutically acceptable carrier, an effective amount of an effective agent according to this invention, and a flavorant. Preferably the effective agent is an aminocarboxylic acid nutrient compound having formula (I). Particularly preferred effective agents are those listed in Table 1.

Preferred flavorants that can be used in a pleasant tasting oral dosage form according to this invention include herbs such as basil, cilantro, dill, oregano, tarragon, and thyme; spices such as cinnamon, clove, ginger, mace, and nutmeg, and essential oils such as oil of lemon, oil of orange, oil of peppermint, and oil of sassafras.

In a particularly preferred pleasant tasting oral dosage form according to this invention, there are present in amounts selected to complement the taste characteristics of each at least one first nutrient compound having the formula $$X-(CH_2)_n-CH(O)_qH-CH-COO^- \quad (II)$$
$$\qquad\qquad\qquad\qquad\qquad |$$
$$\qquad\qquad\qquad\qquad\quad (NH_2+)_pH$$

in which X is selected from the group consisting of $$-NH_2, \quad \text{and} \quad -NH-C=NH,$$
$$\qquad\qquad\qquad\qquad\qquad |$$
$$\qquad\qquad\qquad\qquad\quad NH_2$$

n is two or three, p is one and q is zero, and at least one second nutrient compound having the formula $$X-(CH_2)_n-CH(O)_qH-CH-COO^-$$
$$\qquad\qquad\qquad\qquad\qquad |$$
$$\qquad\qquad\qquad\qquad\quad (NH_2^+)_pH$$

in which X is selected from the group consisting of $$-SH, \quad -CONH_2, \quad -N(CH_3)_3^+, \quad -SCH_3, \quad \text{and}$$

$$-CO-NH-H-CO-NHCH_2CO-OH,$$
$$\qquad\qquad\quad |$$
$$\qquad\qquad CH_2SH$$

n is zero or one, and p and q are each zero or one, provided that p is zero and q is one only when X is $-N(CH_3)_3+$.

In such compositions, the taste characteristics of the first nutrient compound and the second nutrient compound interact in such a way as to produce an overall pleasant tasting composition.

Pleasant tasting tablets in accordance with this invention can be prepared, for example, from 750 milligrams of each of compounds #1, 3, 5, 7, and 8 of Table 1, 5 milligrams each of stearin, magnesium stearate, and magnesium silicate, and 10 milligrams of finely powdered cinnamon.

A pleasant tasting fruit flavored drink in accordance with this invention can be prepared, for example, by blending 4500 milligrams of each of compounds #1, 3, 5, 7, and 8 of Table 1, 110 milliliters of commercially available chilled grapefruit juice, and 5 drops oil of orange.

Pleasant tasting tablets containing a first nutrient compound and a second nutrient compound in accordance with this invention can be prepared, for example, from 500 milligrams of each of compounds #1, 2, 3, 5, 7, and 8 of Table 1, 250 milligrams of each of compounds #4 and 6 of Table 1, and 5 milligrams each of stearin, magnesium stearate, and magnesium silicate.

The following Examples are provided to illustrate the invention without intending to limit its scope, which is defined by the appended claims.

EXAMPLE 1

Quantities of Mexican beer were administered on alternate days on an empty stomach to a female human subject known to be susceptible to headaches believed to be associated with the consumption of imported beer. The following observations were recorded

| Trial | Quantity | Time to onset of headache |
|---|---|---|
| a | Half bottle | 2 hours |
| b | Full bottle | 1 hour |
| c | 2 bottles | ½ hour |

The results show that the quantities of imported beer given in these trials are clearly sufficient to trigger a headache in this individual.

EXAMPLE 2

Quantities of diet cola were administered on alternate days on an empty stomach to a male human subject known to be susceptible to headaches believed to be associated with the consumption of diet cola. The following observations were recorded.

| Trial | Quantity | Time to onset of headache |
|---|---|---|
| a | half of 12 oz can | no headache observed |
| b | full can | 2 hours |
| c | 2 cans | 1 hour |
| d | 3 cans | 45 minutes |
| e | 4 cans | 30 minutes |

The results show that the quantities of diet cola given in trials b through e are clearly sufficient to trigger a headache in this individual.

EXAMPLE 3

Quantities of white wine (fractions of a 750 ml bottle) known to contain sulfites were administered on alternate days on an empty stomach to a male human subject and a female human subject both known to be susceptible to headaches believed to be associated with the consumption of sulfites. The following observations were recorded.

| Trial | quantity | Time to onset of headache |
|---|---|---|
| a | ⅛ bottle | no headache observed |
| b | ¼ bottle | 2 hours |
| c | ½ bottle | 1 hour |
| d | 1 bottle | ½ hour |

The results confirm that the sulfite-containing wine given in trials b, c, and d reproducibly trigger a headache in these individuals. No such effect was noted with wine not containing sulfites.

EXAMPLES 4–5 and COMPARISON TRIALS 1–4

In each of the following trials, a half bottle of sulfite-containing wine was administered to the same subjects as in Example 3. After the onset of headache was noted, approximately one hour after giving the wine, there was administered a dose of a substance as noted below.

| Example no. | Substance | Dose | Time from administration to disappearance of headache |
|---|---|---|---|
| 4 | Blend of substances from Table 1 | 2000 mg | one hour |
| 5 | " | 4000 mg | half hour |
| Comparison 1 | none | | no effect in ten hours |
| Comparison 2 | blend of substances from table 2 | 4000 | no effect in ten hours |
| Comparison 3 | aspirin (three tablets = 975 milligrams) | | 90 minutes |
| Comparison 4 | acetaminophen (1000 milligrams) | | 80 minutes |
| Comparison 5 | ibuprophen (500 milligrams) | | 100 minutes |

The results show the blend of substances shown in Examples 4 and 5 was an effective agent according to this invention in relieving headache triggered by sulfite containing wine in accordance with a method of this invention, and acted more rapidly than conventional pain remedies at doses at or above their maximum recommended level. The results also show that compounds of Table 2 with structural similarity to those effective according to this invention but differing in the assignments of X and/or n in the formula were ineffective.

I claim:

1. A flavorant composition having a reduced tendency to produce a perceptible sensation of pain in a person susceptible to the pain-inducing tendency of monosodium glutamate, consisting essentially of monosodium glutamate and an agent which is at least one nutrient compound having the formula $$X-(CH_2)_n-CH(O)_qH-CH(NH_2^+)_pH-COO-$$

in which X is selected from the group consisting of

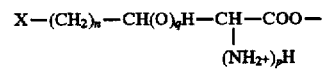

and

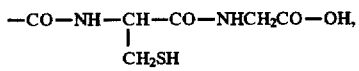

n is zero, one, two, or three, and p and q are each zero or one, provided that p is zero and q is one only when X is $-N(CH_3)_3+$.

2. The flavorant composition of claim 1 in which X is $-SH$ and n is zero.

3. The flavorant composition of claim 1 in which X is $-CONH_2$ and n is one.

4. The flavorant composition of claim 1 in which X is $-SCH_3$ and n is one.

5. The flavorant composition of claim 1 in which X is $-NH_2$ and n is two or three.

6. The flavorant composition of claim 1 in which X is

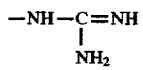

and n is two.

7. The flavorant composition of claim 1 in which X is

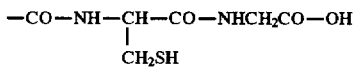

and n is one.

8. The flavorant composition of claim 1 in which X is —N(CH₃)₃+, n is zero, p is zero, and q is one.

9. A flavorant composition according to claim 1, in which the relative proportions of monosodium glutamate to nutrient compound are in the range from 9:1 to 1:9.

10. A sweetener composition having a reduced tendency to produce a perceptible sensation of headache in a person susceptible to the headache-inducing tendency of aspartame, consisting essentially of aspartame and an agent which is at least one nutrient compound having the formula

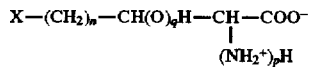

in which X is selected from the group consisting of

—SH, —CONH₂, —N(CH₃)₃⁺, —SCH₃, —NH₂,

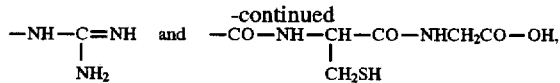

n is zero, one, two, or three, and p and q are each zero or one, provided that p is zero and q is one only when X is —N(CH₃)₃+.

11. The sweetener composition of claim 10 in which X is —SH and n is zero.

12. The sweetener composition of claim 10 in which X is —CONH₂ and n is one.

13. The sweetener composition of claim 10 in which X is —SCH₃ and n is one.

14. The sweetener composition of claim 10 in which X is —NH₂ and n is two or three.

15. The sweetener composition of claim 10 in which X is

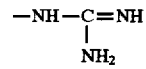

and n is two.

16. The sweetener composition of claim 10 in which X is

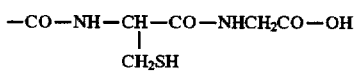

and n is one.

17. The sweetener composition of claim 10 in which X is —N(CH₃)₃+, n is zero, p is zero, and q is one.

18. A sweetener composition according to claim 10, in which the relative proportions of aspartame to nutrient compound are in the range from 9:1 to 1:9.

* * * * *